United States Patent [19]

Boesten

[11] 4,111,980

[45] Sep. 5, 1978

[54] PROCESS FOR PREPARING OPTICALLY ACTIVE PHENYL GLYCINE

[75] Inventor: Wilhelmus H. J. Boesten, Sittard, Netherlands

[73] Assignee: Stamicarbon, B.V., Geleen, Netherlands

[21] Appl. No.: 775,942

[22] Filed: Mar. 9, 1977

[30] Foreign Application Priority Data

Mar. 11, 1976 [NL] Netherlands .......................... 7602544

[51] Int. Cl.$^2$ ............................................ C07C 99/00
[52] U.S. Cl. ................................................... 562/401
[58] Field of Search .................................... 260/518 R

[56] References Cited

U.S. PATENT DOCUMENTS 3,808,254  4/1974  Matthews ............................ 260/590

OTHER PUBLICATIONS

Watanabe et al., Chem. Abst., vol. 80, p. 372, #71099b, (1974).
Chibata et al., Chem. Abst. vol. 83, p. 919, #10843e, (1975).
Chibata et al., Chem. Abst., vol. 82, p. 584, #125609e, (1975).
Hickenbottom, Reactions of Organic Compounds, pp. 334–335, (1957).
Steiger et al., Org.-Syn. Coll., vol. 3, pp. 84–91.

*Primary Examiner*—James O. Thomas, Jr.
*Assistant Examiner*—James H. Reamer
*Attorney, Agent, or Firm*—Cushman, Darby & Cushman

[57] ABSTRACT

A process for preparing optically active phenyl glycine includes treating phenyl glycine amide with optically active camphor sulphonic acid to prepare racemic phenyl glycine, followed by resolution of the racemate by treating the racemate with said camphor sulphonic acid.

3 Claims, No Drawings

PROCESS FOR PREPARING OPTICALLY ACTIVE PHENYL GLYCINE

BACKGROUND OF THE INVENTION

The invention relates to a process for preparing optically active phenyl glycine, that is D-phenyl glycine and/or L-phenyl glycine. D-phenyl glycine is useful as a starting material for the preparation of the antibiotic α-aminobenzyl penicillin, while L-phenyl glycine is useful for the preparation of the sweeting agent L-asparagine-L-phenyl glycine alkyl ester.

Phenyl glycine has been resolved by treatment of racemic phenyl glycine with optically active camphor sulphonic acid, as disclosed in the Journal of American Chemical Society, volume 47, page 1170 (1925). The racemic phenyl glycine is usually prepared by hydrolysis of the corresponding nitrile by treating the nitrile with large excesses of strong acid, such as, e.g., hydrochloric acid, as disclosed in the Journal of American Chemical Society, volume 42, page 2264 (1920).

The disadvantage of the aforementioned procedure for preparing optically active phenyl glycine from the racemic precursor nitrile is the large amount of salts that are produced as by-products, since, after hydrolysis of the nitrile, the hydrolysis mixture must be neutralized with, e.g. ammonia, for the recovery of the phenyl glycine.

In accordance with the invention, it has been discovered that optically active camphor sulphonic acid is not only suitable for effecting the optical resolution of racemic phenyl glycine, but is also suitable for hydrolyzing phenyl glycine amide to phenyl glycine without losses of optical activity. Thereby, much less neutralized acid in the salt form, is obtained as a by-product.

DESCRIPTION OF THE INVENTION

The invention provides a process for preparing optically active phenyl glycine. The improvement of the invention resides in using optically active camphor sulphonic acid to hydrolize racemic phenyl glycine amide, in a process which includes the steps of hydrolizing phenyl glycine amide with acid to form racemic phenyl glycine and of resolving racemic phenylglycine by treating it with optically active camphor sulphonic acid.

The phenyl glycine amide reactant can be prepared in a manner described in the Journal of the Chemical Society, pages 3479–3489 (1951) starting from anhydrous aceton and phenyl glycine nitrile, or in accordance with the non-pre-published Dutch Patent Application No. 7,509,867. These processes for forming the phenyl glycine amide reactant obviate the production of the by-product salt produced when the acid used to hydrolize phenyl glycine nitrile is neutralized.

The hydrolysis of the phenyl glycine amide can be carried out at various temperatures, e.g., a temperature of between 80° and 130° C.

The hydrolysis and the optical resolution can be carried out in a liquid medium in which the diastereo-isomeric salts to be formed are soluble to different extents, for instance in water, water-miscible-solvents and mixtures of water and water-miscible solvents which include, e.g., water, acetic acid, methanol, ethanol, and mixtures of these solvents. In the aforementioned solvents, the salt of D-phenyl glycine with D-camphor sulphonic acid (D-D salt) is much less soluble than the salt of L-phenyl glycine with D-camphor sulphonic acid (L-D salt), while the salt of L-phenyl glycine and L-camphor sulphonic acid (L-L salt) is much less soluble than the salt of D-phenyl glycine with L-camphor sulphonic acid (D-L salt).

In the process according to the invention, racemic phenyl glycine amide is converted into the salts of phenyl glycine and optically active camphor sulphonic acid, while the ammonia salt of the optically active camphor sulphonic acid is formed as a by-product. After separation of the diastereo isomeric salt in the optical resolution, the camphor sulphonic acid can be recovered from that ammonia salt e.g. by reaction with an acid thereby forming a second (other) ammonia salt as a by-product. The amount of this second ammonia salt is appreciably less than the amount of by-product in the prior art discussed above. For practical realization the amount of optically active camphor sulphonic acid used, based on the amount of the reactant racemic phenyl glycine amide to be hydrolized and resolved should be at least two moles per mole of amide. In principle, there is no upper limit for the amount of optically active camphor sulphonic acid to be used in the process according to the invention. An amount of e.g. more than 10 moles of acid per mole of amide has however no practical advantage. Obviously, the hydrolysis of the racemic phenyl glycine amide to racemic phenyl glycine and diastereo-isomeric salt formation of the racemic phenyl glycine can be undertaken simultaneously.

The resulting diastereoisomeric salt can be converted into the optically active phenyl glycine by treating the salt with ammonia water. The ammonia used in this conversion results in the formation of the ammonia salt of the optically active camphor sulphur acid used; the optically active camphor sulphonic acid can be recovered by ion-exchange treatment.

The process outlined above is meant to encompass certain alternative embodiments. One embodiment is directed to maximizing the recovery of one of the enantiomer of phenyl glycine; that is, the embodiment is directed to maximizing the amount of enantiomer recovered from any given amount of racemic phenyl glycine produced in accordance with the process. After recovery of one of the enantiomers of phenyl glycine, the enantiomer which has not been recovered may be racemized. Racemization of the unrecovered enantiomer can be undertaken by heating an aqueous solution of the unrecovered enantiomer in the presence of racemic phenyl glycine amide which is to be hydrolized. Racemization and hydrolysis can be affected in one reactor, without racemization of the optically active camphor sulphonic acid then present. In accordance with this embodiment of the invention, in which the undesired enantiomer is racemized during hydrolysis, the temperature of hydrolysis may range from between 100° to 120° C.

A second embodiment deals with an alternative manner for isolating one diastereoisomeric salt from the other in the above process. In this embodiment, the two diastereoisomeric salts can be dissolved completely. The solvent is then removed, and the remaining solid substance, a mixture of the diastereoisomeric salts, is subjected to preferential extraction with, for instance, water, water-miscibles solvents or water mixed with water-miscible solvents which may be, e.g., water, acetic acid, methanol, ethanol, and mixtures of these solvents. The possibility of realizing preferential extraction is based on the varying solubility properties of the D-D salt compared to the L-D salt and the varying solubility of the L-L salt as compared to the D-L salt, outlined above.

The following examples serve to illustrate the invention as discussed above but are not meant to be limiting, in that the invention contemplates the use of all alternative and equivalents known in the art.

EXAMPLE I

A mixture of 5.0 grams (33.3 mlmoles) of DL-phenyl-glycine amide, 13.2 grams (60.6 mlmoles) of L-phenyl glycine containing 15.5% by weight of D-phenyl glycine, 42.1 grams (172.9 mlmoles) of 95.5% by weight D-camphor sulphonic acid (camphor-10-sulfonic acid), and 57 ml of water are heated at a temperature of 115° C for 12 hours with stirring in an autoclave provided with a stirrer and a heating jacket.

At the end of the 12 hour reaction period, the autoclave is cooled to 40° C, and the resulting crystals are filtered and washed with 7 ml of water. Upon drying at 50° C and 12 mm of Hg, 13.0 grams of D-phenyl-glycine-D-camphor sulphonic-acid salt are obtained.

7.7 grams (20 millimoles) of the D-D salt obtained are taken up in 20 ml of water and neutralized by adding concentrated ammonia, with stirring, to adjust the pH of the aqueous solution 7.5. The resulting D-phenyl glycine is filtered off and washed on the filter with 10 ml of water and 10 ml of methanol. Upon drying at 50° C and 12 mm of Hg, 2.7 grams of D-phenyl glycine is obtained (yield 90%) which has a specific rotation of:
$[\alpha]_D^{20} = -155°$ (C = 1.0; 1 N.HCl).

The specific rotation for optionally pure D-phenyl glycine known from literature (see Netherlands Patent Application No. 7,207,734) is:
$[\alpha]_D^{20} = 156.3°$ (C = 1.0; 1 N.HCl).

Consequently, the optical purity of the D-phenyl glycine is 99.3%.

Ammonia is added to the filtrate obtained from the mixture from the autoclave to adjust the pH of the filtrate to 7. The L-phenyl glycine which then crystallizes is filtered off and washed with 20 ml of water. Upon drying at 50° C and 12 mm of Hg, 12.1 grams of L-phenyl glycine are obtained (yield 95.3%).

EXAMPLE II 1.5 grams (0.01 gmole) of DL-phenyl glycine amide, 5.0 grams of D-camphor sulphonic acid. $H_2O$ (0,02 gmole) and 10 ml of water are mixed in a flask provided with a stirrer and a reflux condenser. The mixture is heated at the boiling temperature (about 102° C) for 16 hours with stirring. Amino-acid analysis of the reaction mixture that has been diluted with 16 ml of water shows that the reaction mixture contains 4.7% by weight of phenyl glycine and 0.1% by weight of phenyl glycine amide. In other words, 98% of the DL-phenyl glycine amide has been hydrolysed.

What is claimed is:

1. In a process for preparing optically active phenyl glycine, in which racemic phenyl glycine is prepared and then optically resolved by treatment with an optically active camphor sulphonic acid, the improvement consisting essentially in treating a racemic phenyl glycine amide solution with an optically active camphor sulphonic acid solution, thereby simultaneously hydrolizing said racemic phenyl glycine amide and forming the diastereo-isomeric salts of phenyl glycine and said optically active camphor sulphonic acid, thereafter separating an enantiomer of the phenyl glycine-camphor sulphonic acid salt, and recovering the optically active phenylglycine enantiomorph therefrom by neutralization.

2. The process according to claim 1, further including the step in which an enantiomer of phenyl glycine is racemized by heating an aqueous solution of said enantiomer together with said phenyl glycine amide to be hydrolized in the presence of an optically active camphor sulphonic acid.

3. The process according to claim 2, wherein said racemization and hydrolysis are undertaken simultaneously at a temperature of between 100° to 120° C.